United States Patent [19]

Perez-Mendez et al.

[11] 4,338,948
[45] Jul. 13, 1982

[54] METHOD AND APPARATUS FOR DETECTING AND/OR IMAGING CLUSTERS OF SMALL SCATTERING CENTERS IN THE BODY

[75] Inventors: Victor Perez-Mendez, Berkeley; Frank G. Sommer, Palo Alto, both of Calif.

[73] Assignee: Regents of the University of California, Berkeley, Calif.

[21] Appl. No.: 134,624

[22] Filed: Mar. 27, 1980

[51] Int. Cl.³ ............................................. A61B 10/00
[52] U.S. Cl. ..................................... 128/660; 73/602; 73/609
[58] Field of Search ............................... 128/660–661; 73/597–598, 602, 609–612, 614, 618–626

[56] References Cited

U.S. PATENT DOCUMENTS

| | | | |
|---|---|---|---|
| 3,052,115 | 9/1962 | Renaut et al. | 73/622 |
| 3,299,694 | 1/1967 | Dickinson | 73/602 |
| 3,426,437 | 2/1969 | Rebhun et al. | 73/622 |
| 3,676,584 | 7/1972 | Plakas et al. | 73/614 |
| 3,924,450 | 12/1975 | Uchiyama et al. | 73/597 |
| 4,074,564 | 2/1978 | Anderson | 73/602 |
| 4,075,883 | 2/1978 | Glover | 73/602 |
| 4,105,018 | 8/1978 | Greenleaf et al. | 73/602 |
| 4,130,112 | 12/1978 | Frazer | 128/660 |
| 4,167,180 | 9/1979 | Kossoff | 73/620 |

OTHER PUBLICATIONS

Wells, P.N.T., "Ultrasonics in Clinical Diagnosis," Churchill-Livingstone Publ., 1977, pp. 6–7, 35, 172–173.

Barbu, Frank E., "Ultrasonic Microprobe," Conference: *Ultrasound in Medicine*, vol. 11, Seattle, Washington U.S.A. (6–10 Oct. 1974).

*Primary Examiner*—Stephen C. Pellegrino
*Assistant Examiner*—Francis J. Jaworski
*Attorney, Agent, or Firm*—Flehr, Hohbach, Test, Albritton & Herbert

[57] ABSTRACT

An ultrasonic method and apparatus are provided for detecting and imaging clusters of small scattering centers in the breast wherein periodic pulses are applied to an ultrasound emitting transducer and projected into the body, thereafter being received by at least one receiving transducer positioned to receive scattering from the scattering center clusters. The signals are processed to provide an image showing cluster extent and location.

10 Claims, 6 Drawing Figures

METHOD AND APPARATUS FOR DETECTING AND/OR IMAGING CLUSTERS OF SMALL SCATTERING CENTERS IN THE BODY

The Government has rights to this invention pursuant to Contract No. W-7405-ENG-48 awarded by the U.S. Department of Energy.

This invention relates generally to a method and apparatus for detecting and/or imaging clusters of small scattering centers in a body and, more particularly, to a method of imaging clusters of calcifications in the breast by ultrasound scattering.

Various types of malignant and benign breast tumors are associated with clusters of calcifications with grain sizes ranging from 0.1 to 2 millimeters or larger. These clusters contain, in some cases, as few as 5 or 6 grains or can contain many tens of grains. The size and shape of these clusters vary from spherical distributions of one centimeter size to elongated distribution spread out over a few centimeters. The correlation between the existence of micro calcification clusters and some form of carcinoma is believed to be greater than 80%. The standard method for detection of these calcifications is mammography which uses an x-ray. The x-ray dose to the patient is appreciable and may be hazardous.

It is a general object of the present invention to provide a non-hazardous method and apparatus for detecting and/or imaging clusters of small scattering centers in a body.

It is another object of the present invention to provide a method and apparatus using ultrasound to detect and/or image clusters of calcification centers in a patient.

It is another object of the present invention to provide an image of calcification centers and their location in the breast employing ultrasonic scattering.

The foregoing and other objects of the invention are achieved by an apparatus which includes a sending ultrasonic transducer, means for applying periodic pulses of electrical energy of predetermined frequency to said transducer whereby ultrasound pulses are projected into the body, at least one receiving transducer adapted to receive ultrasound energy scattered from clusters of scattering centers in the volume of the body and provide output signals and means for receiving and processing the output signals and providing indication or display of the calcification centers. The invention further relates to the method of detecting calcification centers in the human breast which comprises the steps of projecting or directing pulses of ultrasonic energy into the breast, detecting scattered ultrasonic energy from the calcification clusters within the breast and providing output signals and processing the output signals to provide an image showing the extent and location of the clusters.

The foregoing and other objects of the invention will be more clearly understood when taken in connection with the following description and the accompanying drawings.

Figure 4:
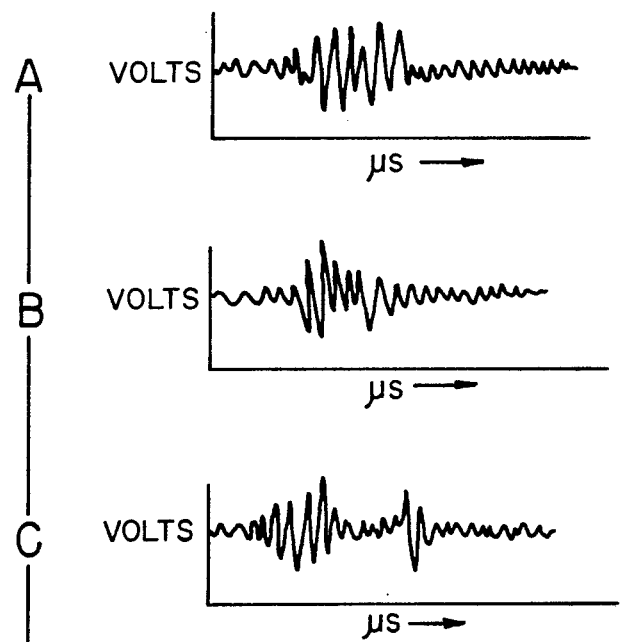

FIGS. 4A-C show signals received at three different scattering angles.

Figure 5:
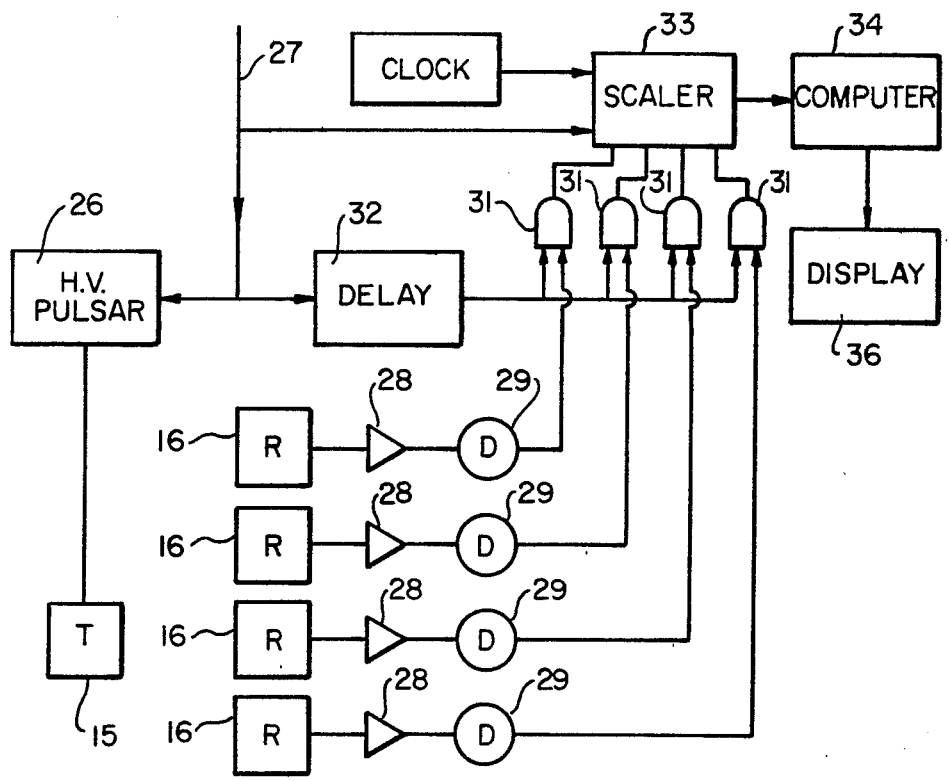

FIG. 5 is a schematic block diagram of a system suitable for carrying out the present invention.

Figure 6:
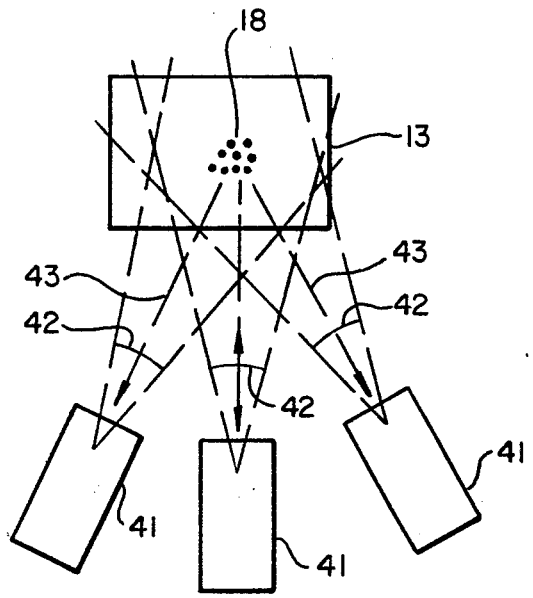

FIG. 6 shows apparatus in accordance with another embodiment of the invention.

Figure 1:
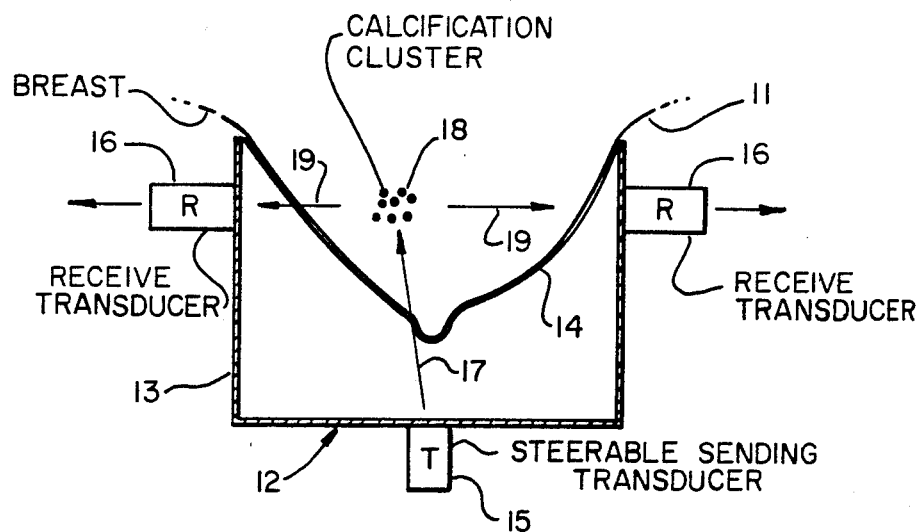
FIG. 1 is a schematic elevational view of an apparatus suitable for carrying out the present invention.
Figure 2:
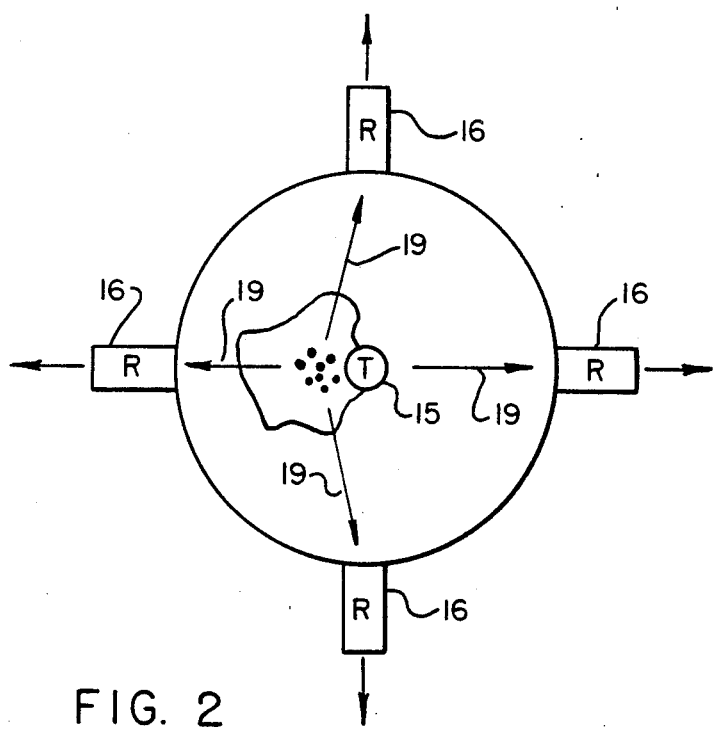
FIG. 2 is a plan view of the apparatus shown in FIG. 1.

Referring to FIGS. 1 and 2, there is shown schematically a human breast 11 associated with apparatus 12 in accordance with the present invention. The apparatus may, for example, comprise container 13 including an upper flexible wall or membrane 14. The container is filled with water or other suitable fluid which couples the ultrasound pulses generated by transmitting transducer 15 to the breast 11. A plurality of receiving transducers 16 are disposed to receive ultrasound energy scattered from inclusions in the breast. In the particular example shown, the receiving transducers are located at 90° with respect to one another. The sending or transmitting transducer is steerable whereby it can scan the breast to locate calcification clusters at any position within the breast. The transmitter sends ultrasound waves indicated by arrow 17 which are scattered by the clusters 18 and travel outwardly as indicated by arrows 19 to the receiving transducers.

Figure 3:
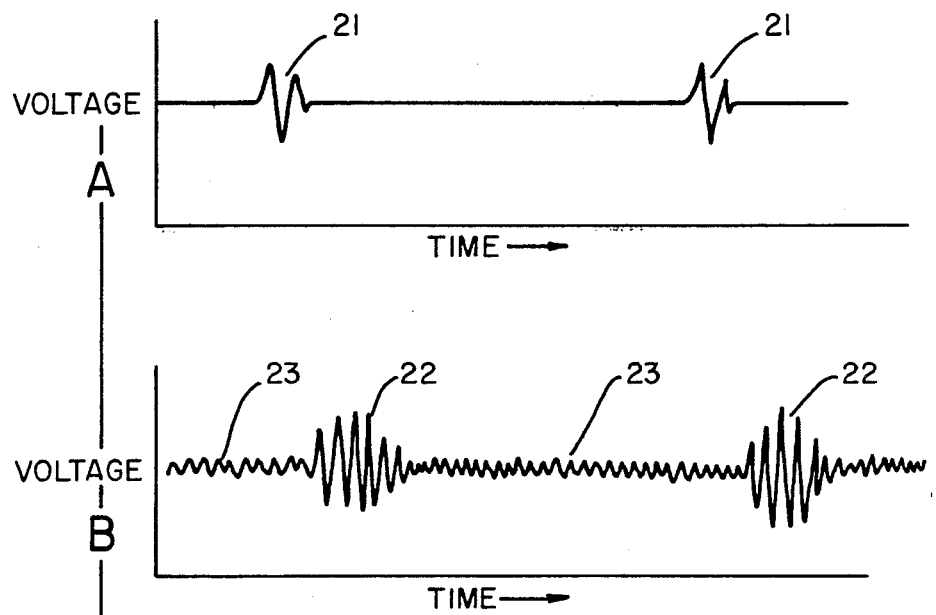
FIG. 3A shows the ultrasound pulses projected into the body.
FIG. 3B shows the received scattered energy.

Referring to FIG. 3A, the periodic pulses of ultrasonic energy transmitted by the steerable transducer are indicated by the envelopes 21. The scattered energy received by one of the transducers is shown by the envelopes 22. The pulses received by the other transducers will be the same except for different delay. The noise at the receiving transducers is shown at 23 and is seen to be less than the received signals whereby the signals can be detected by an amplitude discriminator. The time delay between the transmission of the pulses, FIG. 3A, and receipt of the pulses, FIG. 3B, is an indication of the distance which the ultrasound energy has traveled from the transmitting transducer to the receiving transducer. By employing a plurality of receiving transducers and knowing their location and the time delays, it is possible to pinpoint the location of the calcification cluster by processing the signals simultaneously received by the transducers.

The energy is selected to have a wavelength comparable to the diameter of the particles forming the cluster. In accordance with the well known principle, the sound energy of this wavelength is scattered over a $2\pi$ scattering angle. The scattered sound is of substantially equal intensity in all directions. Thus, all receiving transducers will receive comparable signals modified only by the difference in tissue absorption of the particular path from the scattering center to the transducer. FIGS. 4A-C shows data received at three different angles in an experiment. It is seen that the scattering can be easily detected and that its amplitude is significantly higher than the background noise. Furthermore, it is noted that the received signals are of substantially equal amplitude. The use of multiple transducers enables one to distinguish the smaller scatter signals from the larger interface back reflections. Any specular reflection received by a transducer will have a high amplitude and can be rejected by the associated electronics. The apparatus serves to process only signals having comparable amplitude to thereby reject signals due to reflections from interfaces and the like.

As described, the frequency of the transmitter is selected to have a wavelength comparable to that of the grain size. Other factors that have to be considered in selecting the frequency is that the amplitude of the scattered signals from the grains is a function of their diameter and the average attenuation in the breast tissue. From an acoustical scattering theory, it is known that the short wavelength limit of the sound is when it becomes smaller than the mean diameter of the scattering object. The scattered intensity approaches a constant magnitude independent of the diameter at that point. The higher the frequency, the smaller the particles which can be detected.

By scanning the transmitter and processing the signals, the entire breast volume can be displayed as tomographic images at a series of planes.

FIG. 5 is a schematic diagram of apparatus suitable to carry out the invention. The apparatus includes a high voltage pulser 26 which provides high frequency electrical pulses to the steerable transmitting transducer 15. The pulser is controlled by a strobe signal 27 whereby it applies periodic pulses 21, FIG. 3A, to the transducer.

The plurality of receiving transducers 16 each have their output connected to a tuned amplifier 28 to amplify electrical signals at the transmit frequency and reject other signals. Discriminators 29 are amplitude discriminators which pass signals having amplitudes which are higher than the noise 23. The output of each discriminator is supplied to an AND gate 31 which is controlled by the delayed strobe signal. The strobe signal is delayed by a delayed gate generator 32. A suitable scaler 33 is provided to scale the signals and apply them to computer 34 which then processes the signals from the receiving transducers to provide a display 36 showing the location and size of the clusters. The computer processes the signals by a combination of transit time comparison and receiver transducer array positioning. The output of the computer provides at the display 36 a tomographic image.

FIG. 6 shows another embodiment of the invention. In this embodiment the transducers act both as sending and receiving transducers by being switched between modes. Referring more particularly to the figure, there is shown a plurality of transducers 41 operating in a pulse echo mode (each acts as a sending and receiving transducer). Each of the transducers projects a fan beam 42 of ultrasonic energy with the beams overlapping. The scattered received energy from the clusters 18 is shown by the arrows 43. Only one of the transducers need be a pulse-echo transducer.

The signals are processed in the manner just described to provide a tomograph. That is, the position and time delay of scattered signals can be processed to provide an image of the clusters 18.

It is apparent that a single transducer may be used in the pulse-echo mode and positioned to a plurality of angles to obtain several scans. This would require memory to retain the results of the scans for processing.

Thus, there is provided a method and apparatus which employs sound signals scattered from clusters of calcifications, processes the scattered signals to distinguish the signals from noise, reflections and the like, correlates the signals and provides a tomographic display or image.

We claim:

1. An apparatus for detecting clusters of scattering centers in a volume of a body, comprising: means for directing ultrasonic energy towards a given cluster of scattering centers in periodic bursts of ultrasonic energy at a predetermined frequency; means for receiving some of said directed ultrasonic energy at a plurality of different points circumferentially spaced around said body after said energy has come in contact with said cluster of scattering centers, said receiving means distinguishing between received ultrasonic energy having substantially the same, common amplitude at the various receiving points from received ultrasonic energy having differing amplitudes at the various receiving points, whereby to distinguish scattered ultrasonic energy having substantially the same amplitude at all of the receiving points from noise or reflected ultrasonic energy; and means responding only to the scattered ultrasonic energy received and distinguished by said receiving means for producing a corresponding output signal.

2. Apparatus as in claim 1 where the predetermined frequency has a wavelength of the same order of magnitude as the size of the scattering centers.

3. Apparatus as in claim 1 together with means for receiving and processing said output signal and for receiving the processed signal and displaying an image of the clusters.

4. Apparatus as in claim 1 wherein said receiving means includes a plurality of receiving transducers disposed at different positions in a plane and directed to receive the scattered ultrasound energy for providing said output signal.

5. Apparatus as in claim 4 including means for receiving and processing said output signal to provide an image of the clusters and their location.

6. Apparatus as in claim 1 wherein said means for processing said signal and providing an indication of said clusters indicates the size and location of said clusters.

7. An apparatus according to claim 1 wherein said receiving points are located at selected angles around said body between 20° and 170° with respect to said directing means.

8. An apparatus according to claim 1 wherein said ultrasonic energy directing means is positioned at a fixed location relative to said body and wherein said receiving means includes separate receivers at selected angles around said body between 20° and 170° with respect to said ultrasonic energy directing means.

9. An apparatus for detecting clusters of scattering centers in a volume of a body comprising: a steerable transmitting transducer for receiving electrical high frequency pulses and emitting pulses of ultrasonic energy at a predetermined frequency into said body in response to the pulses; means including a plurality of spaced receiving transducers positioned around said body to receive said ultrasonic energy after the latter has come in contact with said clusters of scattering centers and circuitry for distinguishing between received energy having substantially the same, common amplitude at the various transducers from energy of varying amplitude at the various transducers and for generating electrical signals corresponding to the ultrasonic energy having said common amplitude, whereby said generated signals correspond to scattered ultrasonic energy as opposed to noise or reflected ultrasonic energy; and means for receiving and processing said signals to provide indications of said clusters.

10. A method of detecting clusters of scattering centers in a volume of material, comprising: directing ultrasonic energy towards a given cluster of scattering centers in periodic bursts of ultrasonic energy at a predetermined frequency; receiving some of said directed ultrasonic energy at a plurality of different points circumferentially spaced around said body after said energy has come in contact with said cluster of scattering centers;

distinguishing between received ultrasonic energy having substantially the same, common amplitude at the various receiving points from received ultrasonic energy having differing amplitudes at various receiving points, whereby to distinguish scattered ultrasonic energy having substantially the same amplitude at all of the receiving points from noise or reflected ultrasonic energy; and responding only to the scattered ultrasonic energy received and distinguished for producing a corresponding output signal.

* * * * *